United States Patent
Kanda et al.

(10) Patent No.: US 9,216,468 B2
(45) Date of Patent: Dec. 22, 2015

(54) METHOD FOR BRAZING ALUMINUM MEMBERS AND BRAZING APPARATUS USED FOR SAME

(75) Inventors: Kiichi Kanda, Kanagawa (JP); Kenichi Watanabe, Kanagawa (JP); Yutaka Yanagawa, Tokyo (JP)

(73) Assignees: Kanto Yakin Kogyo Co., Ltd., Kanagawa (JP); Furukawa-Sky Aluminum Corp., Tokyo (JP)

( * ) Notice: Subject to any disclaimer, the term of this patent is extended or adjusted under 35 U.S.C. 154(b) by 0 days.

(21) Appl. No.: 13/880,777

(22) PCT Filed: Oct. 26, 2011

(86) PCT No.: PCT/JP2011/074660
§ 371 (c)(1),
(2), (4) Date: Apr. 22, 2013

(87) PCT Pub. No.: WO2012/057197
PCT Pub. Date: May 3, 2012

(65) Prior Publication Data
US 2013/0221077 A1    Aug. 29, 2013

(30) Foreign Application Priority Data

Oct. 28, 2010  (JP) .................. 2010-242744

(51) Int. Cl.
*B23K 1/00* (2006.01)
*B23K 1/19* (2006.01)
(Continued)

(52) U.S. Cl.
CPC . *B23K 1/19* (2013.01); *B23K 1/008* (2013.01); *B23K 1/0012* (2013.01); *B23K 35/002* (2013.01); *B23K 35/284* (2013.01);
(Continued)

(58) Field of Classification Search
CPC .. B23K 35/286; B23K 1/008; B23K 2201/14; B23K 35/0238; B23K 1/19; B23K 2203/10; B23K 35/002; B23K 35/38; B23K 1/012; B23K 35/284; B23K 35/001
USPC .......................................... 228/262.5, 262.51
See application file for complete search history.

(56) References Cited

U.S. PATENT DOCUMENTS 3,378,914 A * 4/1968 Miller ........................... 228/193
5,911,357 A * 6/1999 Takahashi ..................... 228/214
(Continued)

FOREIGN PATENT DOCUMENTS

JP    3-297592 A    12/1991
JP    6-000686 A    1/1994
(Continued)

*Primary Examiner* — Erin Saad
(74) *Attorney, Agent, or Firm* — Carrier Blackman & Associates, P.C.; William D. Blackman; Joseph P. Carrier

(57) ABSTRACT

Provided are: a method for brazing an aluminum alloy, which is characterized in that brazing is carried out by heating an aluminum brazing sheet without using flux in a furnace that is in an argon gas-containing atmosphere, said aluminum brazing sheet comprising a core material that is composed of aluminum or an aluminum alloy and a brazing filler material that is composed of an aluminum alloy and clad on one surface or both surfaces of the core material, and said core material and/or said brazing filler material containing Mg; and a brazing apparatus which is used in the method for brazing an aluminum alloy. The brazing method has good and stable brazing properties and is applicable in industrial practice.

9 Claims, 1 Drawing Sheet

(51) Int. Cl.
*B23K 1/008* (2006.01)
*B23K 35/00* (2006.01)
*B23K 35/28* (2006.01)
*B23K 35/38* (2006.01)
*G01J 3/443* (2006.01)
*G01N 21/67* (2006.01)
*F28F 21/08* (2006.01)
*B32B 15/01* (2006.01)

(52) U.S. Cl.
CPC ............. *B23K35/286* (2013.01); *B23K 35/383* (2013.01); *B32B 15/016* (2013.01); *F28F 21/084* (2013.01); *F28F 21/089* (2013.01); *G01J 3/443* (2013.01); *G01N 21/67* (2013.01); *B23K 2201/006* (2013.01); *B23K 2201/14* (2013.01); *B23K 2203/10* (2013.01)

(56) References Cited

U.S. PATENT DOCUMENTS

| | | | | |
|---|---|---|---|---|
| 6,106,281 | A | * | 8/2000 Materna | 432/198 |
| 2003/0099856 | A1 | * | 5/2003 Takeno et al. | 428/654 |

FOREIGN PATENT DOCUMENTS

| | | | |
|---|---|---|---|
| JP | 9-085433 | A | 3/1997 |
| JP | 10-180489 | A | 7/1998 |
| JP | 2007-044713 | A | 2/2007 |
| JP | 2007-190574 | A | 8/2007 |

* cited by examiner

METHOD FOR BRAZING ALUMINUM MEMBERS AND BRAZING APPARATUS USED FOR SAME

TECHNICAL FIELD

The present invention relates to a method for brazing an aluminum alloys without using flux, and more particularly to a brazing method suitable for manufacturing a heat exchanger.

BACKGROUND ART

Because of having high thermal conductivity and being lightweight, aluminum alloys are used in many heat exchangers which are mounted on automobiles, etc. A heat exchanger for exchanging heat by circulating fluid, e.g., water or oil therein is composed of various parts, such as a tank, tubes, and fins. Those parts are metallically joined to each other by brazing.

As aluminum alloy parts constituting the heat exchanger that are joined by brazing, brazing sheets are used. The brazing sheet comprises an aluminum alloy serving as a core and a filler material clad on one surface or both surfaces of the core alloy. Generally, an aluminum alloy having a melting temperature of 600° C. or higher is used as a core alloy of the brazing sheet, and an Al—Si based alloy having a melting temperature of 600° C. or lower is used as a cladding filler alloy. The heat exchanger can be manufactured through the steps of: forming individual parts of the heat exchanger by employing brazing sheets; combining the individual parts with one another; and heating them to temperature about 600° C. such that only filler alloys of the brazing sheets are melted to join the individual parts to one another. Since many parts constituting the heat exchanger can be joined at a time by employing the brazing sheets for the constituting parts, the brazing sheets are widely used as materials of various parts of the heat exchangers.

Main examples of brazing methods having been practiced so far are vacuum brazing and Nocolok brazing. The vacuum brazing employs a filler material made of an Al—Si—Mg based alloy. By heating parts to be joined in vacuum, Mg in the filler alloys is evaporated and, at that time, oxide films on the surfaces of the filler alloys are broken, thus enabling the brazing. However, the vacuum brazing is disadvantageous in requiring an expensive vacuum heating apparatus. On the other hand, the Nocolok brazing employs a filler material made of an Al—Si based alloy. After coating flux, the flux coated parts to be brazed are heated in an inert gas such that the flux breaks oxide films on the surfaces of the filler alloys, thus enabling the brazing. However, if the flux is coated unevenly, a brazing failure is caused. It is hence required to evenly coat the flux over regions where the brazing needs to be carried out.

Meanwhile, there are proposed brazing methods capable of carrying out the brazing through heating the parts to be joined in an inert gas without using the expensive vacuum heating apparatus and the flux. Patent Document 1 as listed below describes a method of brazing without using flux, the method comprising the steps of veiling the parts to be brazed containing Mg with a carbonaceous cover and heating the parts under the carbonaceous cover in an inert gas atmosphere. According to the method of the Patent Document 1, Mg acts to lower an oxygen concentration in the inner space of the carbonaceous cover and prevent oxidation of the parts placed under the carbonaceous cover, thereby enabling the brazing. Patent Document 2 as listed below describes a method of constructing a heat exchanger by employing a cladding alloy containing Mg as a filler material such that the brazing can be carried out without using flux. According to the method of the Patent Document 2, Mg in the filler material acts to remove oxide films on the surfaces of the filler material, thereby enabling the brazing.

According to any of these brazing methods without using flux, the brazing can be effectuated with Mg contained in the clad alloy and/or the filler alloy and acting to break oxide films. However, those brazing methods are difficult to realize a stable brazeability because the action of Mg breaking oxide films is weaker than those obtained with the vacuum brazing and the Nocolok brazing. The brazeability can be improved by lowering the oxygen concentration in a furnace. It is, however, difficult to maintain a low oxygen atmosphere on the industrial basis.

LIST OF THE PRIOR ART

Patent Documents

Patent Document 1: JP 2007-044713 A
Patent Document 2: JP 2007-190574 A

SUMMARY OF THE INVENTION

Problems to be Solved by the Invention

An object of the present invention is to provide a brazing method utilizing the action of Mg breaking oxide films and using no flux, which brazing method has a more satisfactory and stable brazeability. The brazing method is industrially applicable as well.

Means for Solving the Problems

As a result of conducting intensive studies in view of the problems described above and focusing attention to the fact that what type of atmosphere gas is used in a brazing step imposes a great influence upon the brazeability, the inventors have found that more satisfactory brazeability can be achieved by employing argon gas as the atmosphere gas.

According to a first aspect of the present invention, there is provided a method for brazing aluminum members, the method being characterized by the step of: heating the aluminum members to braze them without using flux in an argon gas-containing atmosphere in a furnace, wherein the aluminum member comprises a brazing sheet that includes a core made of aluminum or an aluminum alloy and a filler material made of an aluminum alloy and clad on one surface or both surfaces of the core, at least one of the core and the filler material containing Mg.

According to a second aspect of the present invention, given that a ratio of luminous intensity of a nitrogen atom to luminous intensity of an oxygen atom, measured by a glow discharge optical emission spectrometry, is defined as a luminous intensity ratio (N/O) and that the luminous intensity ratio (N/O) indicating a constant value at the interior of the filler alloy after having been subjected to the brazing is 1.0, the luminous intensity ratio (N/O) near the surface of said filler material up to the depth where the constant value is indicated, is 1.2 or less.

According to a third aspect of the present invention, the argon gas-containing atmosphere in the furnace is an argon gas atmosphere or a mixed gas atmosphere of argon gas and nitrogen gas, with an oxygen concentration in the furnace being 25 ppm or lower.

According to a fourth aspect of the present invention, there is provided a brazing apparatus used for carrying out the brazing method according to the first to third aspects.

Advantageous Effect of the Invention

The brazing method of the present invention can provide a satisfactory brazeability without using flux by utilizing the action of Mg breaking the oxide film. Since the brazing method of the present invention provides a stable brazeability, it can be suitably applied to industrial uses as well.

EMBODIMENTS FOR CARRYING OUT THE INVENTION

Figure 1:
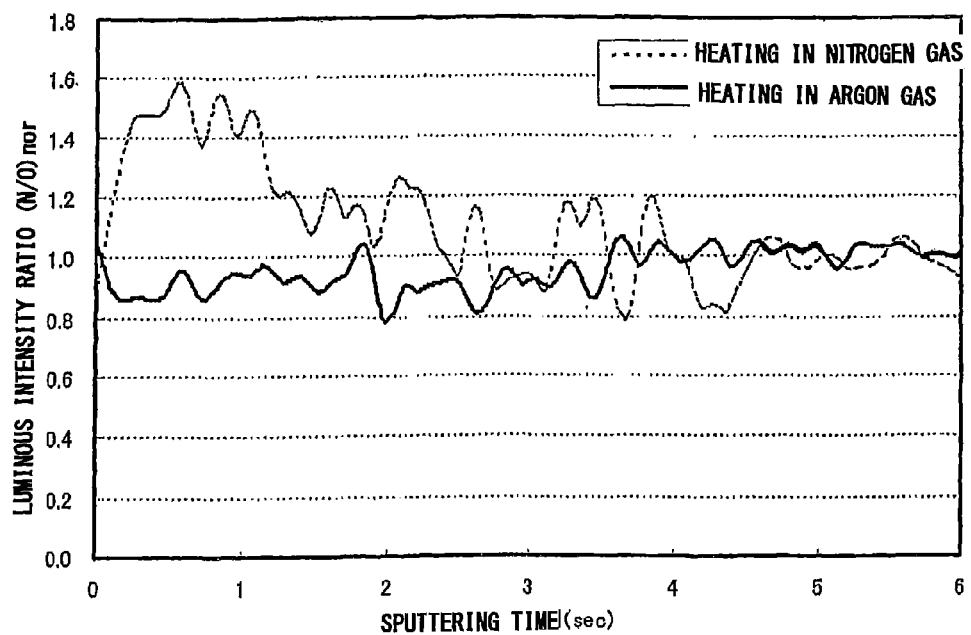
FIG. 1 is a graph showing the relationship between a sputtering time and a luminous intensity ratio (N/O)nor in a filler material after having been subjected to brazing.

The present invention will be described in detail below.

A. Brazing Sheet

First, a brazing sheet used in the brazing method according to the present invention will be described.

The brazing sheet used in the present invention includes a core made of an aluminum alloy, and a filler metal made of an aluminum alloy and clad on one surface or both surfaces of the core. In other words, two types of brazing sheets are used, one type having a two-layer structure in which the filler alloy is clad on the one surface of the core, and the other type having a three-layer structure in which the filler alloy is clad on both the surfaces of the core. A clad ratio of the filler alloy is 2 to 30% per surface. A thickness of the brazing sheet is 0.1 to 3 mm in the two-layer structure and 0.05 to 3 mm in the three-layer structure.

In addition to the above-described forms, the brazing sheet may be of other structures, e.g., a three-layer structure of skin/filler/core in which the skin is additionally clad, a five-layer structure of skin/filler/core/filler/skin, and a three-layer structure of filler/core/sacrificial anode material in which the sacrificial anode material is additionally clad. In those forms, Mg is contained in at least one of the core and the filler metal.

In the present invention, Mg is contained in at least one of the core and the filler metal to utilize the action of Mg breaking an aluminum oxide film. (1) When Mg is contained in the filler metal, the Mg contained in the filler metal deoxidizes and breaks the oxide film on the surface of the filler metal during a temperature rise due to heating for the brazing. (2) when Mg is contained in the core, the Mg diffuses from the core into the filler metal and deoxidizes and breaks the oxide film on the surface of the brazing filler metal during a temperature rise due to heating for the brazing. (3) When Mg is contained in both the core and the filler metal, both the processes described above in (1) and (2) occur.

When Mg is contained in the aluminum alloy of the filler metal, the content of Mg is preferably 0.5 to 2.0 mass % (hereinafter simply denoted as "%"). If the content of Mg is less than 0.5%, the effective action of Mg breaking the oxide film cannot be obtained to thereby degrade the brazeability of the brazing sheet. On the other hand, if the content of Mg is more than 2.0%, an excessive amount of Mg diffuses onto the surface of the filler meal during the heating for the brazing. Since a large amount of Mg remains on the surface of the filler metal without being evaporated therefrom, an oxide film of MgO is formed on the filler metal surface in a relatively large thickness to thereby degrade the brazeability of the brazing sheet.

When Mg is contained in the aluminum alloy of the core, the content of Mg is preferably 0.15 to 2.5%. If the content of Mg is less than 0.15%, an amount of Mg diffusing into the filler metal of the brazing sheet is reduced during the heating step for the brazing. Since a sufficient amount of Mg is not obtained, the brazeability of the brazing sheet becomes deteriorated. On the other hand, if the content of Mg is more than 2.5%, an excessive amount of Mg diffuses into the filler metal from the core during the heating step for the brazing. As a result, an oxide film of MgO is formed on the filler metal surface in a relatively large thickness, as described above, whereby the brazeability of the brazing sheet is degraded.

When Mg is contained in the aluminum alloys of both the filler metal and the core, the content of Mg in the filler metal is preferably 0.1 to 1.4% with the content of Mg in the core being preferably 0.15 to 1.2%. If the content of Mg in the filler metal is less than 0.1%, or if the content of Mg in the core is less than 0.15%, a sufficient amount of Mg cannot be obtained, whereby the brazeability of the brazing sheet becomes deteriorated. On the other hand, if the content of Mg in the filler alloy is more than 1.4%, or if the content of Mg in the core is more than 1.2%, an excessive amount of Mg diffuses onto the surface of the filler metal during the heating step for the brazing. As described above, under these circumstances an oxide film of MgO is formed on the filler metal surface in a relatively large thickness. This degrades the brazeability of the brazing sheet.

From the viewpoint of strength and anticorrosion characteristics of the materials of the brazing sheet, other elements than Mg may be added to the core on condition that those elements are not melted at brazing temperature. Examples of those elements include Si, Fe, Mn, Ni, and Cu from the viewpoint of increasing the material strength. Moreover, Zn, Sn, In, etc. may be added to give the brazing sheet with a sacrificial anticorrosion effect and to increase corrosion resistance.

As adding elements other than Mg, the filler metal may contain known elements that are usually contained in the filler metal. An Al—Si based aluminum alloy containing 7.0 to 13.0 weight % of Si is suitably provided as a typical filler metal containing such an element. A filler metal added with a different element, e.g., Zn or Cu, other than Si can also be used to adjust the melting point and the electric potential of the brazing sheet.

B. Influence of Atmosphere Gas Upon Brazeability

With the method for brazing the brazing sheet of aluminum alloy containing Mg without using flux, the brazing is enabled by the action of Mg to break an oxide film on the surface of the aluminum alloy. Inert gas is used as atmosphere gas. While nitrogen gas or argon gas is usually used, the nitrogen gas that is more inexpensive is commonly used. However, when the brazing sheet of aluminum alloy containing Mg is heated for brazing in the nitrogen gas, a stable brazeability cannot be obtained in some cases. The action of Mg breaking the oxide film is so weak that the oxide film is not broken enough or that the surface of the aluminum alloy having been partially and temporarily exposed upon breakage of the oxide film is re-oxidized. In view of the above, the inventors have examined the brazeability of the brazing sheet in an atmosphere at a lower oxygen concentration, aiming to achieve stable brazeability of the brazing sheet with Mg which exerts its oxide film breaking action enough. As a result, it has been found that the heating step carried out in the lower oxygen atmosphere improves the brazeability of the brazing sheet slightly. However, it has been also found that the improvement is not so remarkable and that there is a limit to a lower oxygen atmosphere being kept in a furnace during a brazing process on the industrial basis in view of the facts that an apparatus which can achieve such brazing process will become complicated and require higher maintenance cost.

Next, the inventors have conducted studies on use of the argon gas as the inert gas instead of the nitrogen gas. Aluminum alloy was heated and brazed in the argon gas atmosphere wherein an oxygen concentration in the furnace was set at the same value as that in the case using the nitrogen gas. As a result, it has been found that the brazeability was greatly improved and stable brazing can be achieved. Based on this finding, the inventors have studied what factor contributes improvement of the brazeability in the brazing using the argon gas. It has been found that, even at the same oxygen concentration, there is a difference between the aluminum alloy heated in the nitrogen gas and that heated in the argon gas in properties of the brazing alloy near its surface after heating in the brazing process. More specifically, near the surface of the brazing alloy heated in the nitrogen gas, accumulation of nitrogen was observed and based on which the presence of a reaction product of aluminum and nitrogen was estimated.

Further studies have resulted in the following supposition. With heating of aluminum alloys in the nitrogen gas, the oxide films on the surfaces of the aluminum alloys are reduced and broken by Mg, and the metal aluminum surface is exposed to the nitrogen atmosphere. The exposed metal aluminum reacts with the nitrogen gas as the atmosphere gas, and a reaction product is formed near the surface of the aluminum alloy. It is reasonable to infer that the reaction product is in the form of a film made of nitrogen and aluminum which degrades the brazeability because such a film of nitrogen and aluminum is no longer broken by Mg.

In contrast, when the aluminum alloy is heated in the argon gas, the surface of the metal aluminum is similarly exposed to the argon gas after the oxide film of aluminum has been broken by Mg. On the exposed surface of the metal aluminum, however, reaction with argon does not occur due to a very low reactivity of argon, and thus a reaction product deteriorating the brazeability is not produced on the heated aluminum alloy. It is hence reasonable to infer that satisfactory brazeability is achieved. In the Nocolok brazing using flux, because the surface of the metal aluminum, after the oxide film has been broken by the flux, is contacted with the atmosphere gas with the flux interposed therebetween, any influence upon the brazeability does not appear regardless of whether the nitrogen gas or the argon gas is used. In the brazing without using flux, however, a great effect in improving the brazeability is obtained by employing the argon gas instead of the nitrogen gas.

The inventors have examined the film-like reaction product of the exposed metal aluminum and the nitrogen gas. In more detail, the examination has been carried out by measuring luminous intensities of a nitrogen atom and an oxygen atom with a glow discharge optical emission spectrometer over a span from the surface of a filler alloy to the interior thereof after brazing process. Stated another way, the luminous intensities of a nitrogen atom and an oxygen atom have continuously been measured from the surface toward the interior of the filler alloy on a sputtered surface while the filler alloy is sputtered.

As a result of calculating a ratio of the luminous intensity of a nitrogen atom to the luminous intensity of an oxygen atom, i.e., "luminous intensity of a nitrogen atom/luminous intensity of an oxygen atom" (hereinafter referred to as a "luminous intensity ratio (N/O)"), at each sputtering time, it has been experimentally found that the luminous intensity ratio (N/O) takes a constant value after the sputtering time exceeds a predetermined time, i.e., at the interior of the filler alloy deeper than a predetermined depth. Such a tendency similarly appears for all filler alloys subjected to the brazing under various conditions. However, the sputtering time at which the luminous intensity ratio (N/O) becomes constant differs depending on the alloy composition of each filler alloy and the brazing conditions. It is to be noted that the expression "constant value" used here does not mean a complete constant value having no deviation, but it may include a deviation of about ±10%.

In order to more clarify the relationship between the sputtering time and the luminous intensity ratio (N/O), the constant value of the luminous intensity ratio (N/O) after the sputtering time exceeds the predetermined time is normalized to a value of "1.0", and the luminous intensity ratio (N/O) at each sputtering time is also normalized at the same proportion. The luminous intensity ratio (N/O) calculated through such normalization is denoted by a "luminous intensity ratio (N/O)nor". FIG. 1 is a graph showing an example of the relationship between the sputtering time and the luminous intensity ratio (N/O)nor. In FIG. 1, the horizontal axis represents the sputtering time, and the sputtering time 0 (sec) corresponds to the surface of the filler alloy. With the lapse of the sputtering time, the depth from the surface of the filler alloy increases. The sputtering time and the sputtering depth from the surface of the filler alloy are proportional to each other. The vertical axis represents the luminous intensity ratio (N/O)nor.

As seen from FIG. 1, in respect of the filler alloy which have been subjected to the brazing in the nitrogen gas, the luminous intensity ratio (N/O)nor at the sputtering time shorter than 4.6 (sec) has a maximum value of 1.6 while the luminous intensity ratio (N/O)nor at the sputtering time of 4.6 (sec) or longer is 1.0. This indicates that, in the filler alloy subjected to the brazing in the nitrogen gas, a presence ratio of the nitrogen atom to the oxygen atom near the surface of the filler alloy is 60% at maximum larger than at the interior thereof where the luminous intensity ratio (N/O) becomes constant. It is hence confirmatively estimated that the above-described film-like reaction product of the metal aluminum and the nitrogen gas is produced near the surface of the filler alloy.

FIG. 1 also shows that, in the filler alloy which has been subjected to the brazing in the argon gas, the luminous intensity ratio (N/O) becomes constant at the sputtering time of 4.6 (sec) or longer similarly to the case using the nitrogen gas. Relative to the luminous intensity ratio (N/O)nor normalized to 1.0 at the sputtering time of 4.6 (sec) or longer, the luminous intensity ratio (N/O)nor at the sputtering time shorter than 4.6 (sec) is mostly 0.8 to 1.0 and its maximum value is about 1.05 even though exceeding 1.0. This indicates that, in the filler alloy which has been subjected to the brazing in the argon gas, a presence ratio of the nitrogen atom to the oxygen atom near the surface of the filler alloy is generally smaller than at the interior thereof where the luminous intensity ratio (N/O) becomes constant. It is hence confirmatively estimated that the film-like reaction product of the metal aluminum and the nitrogen gas, which is produced with the brazing in the nitrogen gas, is not produced near the surface of the filler alloy during the brazing in the argon gas.

The inventors have examined the luminous intensity ratio (N/O)nor near the surface of the filler alloy up to a certain depth under various conditions relative to the luminous intensity ratio (N/O)nor at the interior which is normalized to 1.0.

As a result, it has been found that, when the luminous intensity ratio (N/O)nor is 1.2 or less, the production of the film-like reaction product of the metal aluminum and the nitrogen gas near the surface of the filler alloy is suppressed and the brazeability is not deteriorated.

The argon gas is more expensive than the nitrogen gas. In order to employ the brazing method according to the present invention on the industrial basis, therefore, an amount of argon gas needs to be reduced when the argon gas is used in a furnace conventionally employed for the Nocolok brazing. The amount of argon gas introduced to the furnace is preferably reduced to such an extent as not raising an oxygen concentration. The amount of argon gas introduced can be reduced by employing a brazing furnace of higher gas-tightness. Using a gas mixture of nitrogen and argon and reducing a rate of the argon gas is also useful to further reduce the amount of argon gas used. By using a gas mixture of the nitrogen gas and the argon gas at a volume ratio of 1:1, for example, an amount of the reaction product of aluminum and nitrogen can be suppressed to about a half that produced in the case using the nitrogen gas. This is also effective in improving the brazeability.

C. Influence of Oxygen Gas Upon Brazeability

Even in the brazing in the argon gas without using flux, if the oxygen concentration in the furnace is high, the brazeability degrades because the surface of the aluminum alloy is re-oxidized. The oxygen concentration in the furnace is preferably held at 25 ppm or lower from the viewpoint of obtaining the satisfactory brazeability. If the oxygen concentration in the furnace exceeds 25 ppm, the surface of the aluminum alloy tends to easily oxidize and the brazeability degrade. The oxygen concentration in the furnace is more preferably 10 ppm or lower.

To achieve a lower-oxygen atmosphere, internal components of the brazing furnace, which contact the argon gas, are preferably made of carbon materials. Examples of the internal components of the brazing furnace include a furnace inner wall, a baffle, a mesh belt for conveying objects being brazed, etc. All or a part of those members is made of the carbon material. The carbon material reacts with oxygen present in a minute amount in the argon gas and produces CO, thus lowering the oxygen concentration in the furnace. When the brazing is carried out in the existing brazing furnace, the carbon material may separately be disposed within the furnace.

D. Brazing Apparatus

A brazing apparatus according to the present invention is used for carrying out the above-described brazing method. A furnace adapted to perform the heating for the brazing is preferably capable of controlling the oxygen concentration in the furnace such that it is held at 25 ppm or lower as described above. Moreover, from the viewpoint of achieving the lower oxygen atmosphere, it is also preferable, as described above, to use a brazing apparatus provided with a furnace in which internal components contacting the argon gas are made of carbon materials.

A minute amount of oxygen is introduced into the furnace primarily along with an entry of the object to be brazed. In particular, when a hollow structure is present inside the object to be brazed like a heat exchanger, oxygen existing inside the object is not sufficiently replaced, thus impeding reduction of the oxygen concentration in the atmosphere within the furnace. Therefore, the heating for the brazing in the atmosphere at a lower oxygen concentration can be realized by employing a brazing apparatus that includes a plurality of furnace chambers, such as a chamber for introducing the object to be brazed, a preliminary heating chamber, and a heating chamber for the brazing. The concentration of oxygen which is present inside the object to be brazed can be sufficiently lowered, for example, during a preliminary heating in the preliminary heating chamber.

Furthermore, a rise of the oxygen concentration in the furnace can be prevented by evacuating the furnace into vacuum after introducing the object to be brazed into the furnace, and then by blowing the argon gas into the furnace for replacement of the atmosphere gas in the furnace. To that end, the brazing apparatus used here is preferably further provided with a device for replacing the atmosphere gas in the furnace. That type of brazing apparatus is useful from the industrial point of view because stable brazeability can be achieved in a shorter time.

E. Brazing Conditions

Conditions for the brazing method according to the present invention can be set in accordance with the conditions generally used for the brazing. A time required to reach the melting temperature of the filler alloy is 10 to 30 minutes. A brazing temperature is not lower than the melting temperature of the filler alloy and is usually 590 to 610° C. though it differs depending on the composition of the filler alloy. A holding time at the brazing temperature is usually 3 to 10 minutes.

EXAMPLES

The present invention will be described below in connection with Examples and Comparative Example.

Examples 1 to 11 and Comparative Example 1

A brazing sheet was fabricated in accordance with an ordinary method in which a core was formed of a bare sheet specified in JIS A3003 with the addition of 0.5% of Mg or without addition of Mg, while a filler alloy specified in JIS A4045 with or without addition of Mg was clad on one surface of the core. More specifically, ingots for the core alloy and the filler alloy having alloy compositions listed in Table 1 were cast and subjected to machined finish, respectively. Then, the filler alloy was hot-rolled. The hot-rolled filler alloy was again hot-rolled together with the core alloy. The hot-rolled combination of the filler alloy and the core alloy was next cold-rolled to thereby fabricate the brazing sheets of No. 1 to 11 in Table 1, each being a combination of the core alloy and the filler alloy. A thickness of each brazing sheet was 0.75 mm, and a clad ratio of the filler alloy was 10%.

TABLE 1

| Brazing Sheet No. | Alloy Composition of Core (mass %) | | | | | | Alloy Composition of Filler alloy (mass %) | | | |
|---|---|---|---|---|---|---|---|---|---|---|
| | Si | Mg | Fe | Cu | Mn | Al | Si | Mg | Fe | Al |
| 1 | 0.2 | 0.1 | 0.5 | 0.15 | 1.1 | rest | 10 | 0.0 | 0.4 | rest |
| 2 | 0.2 | 0.2 | 0.5 | 0.15 | 1.1 | rest | 10 | 0.0 | 0.4 | rest |
| 3 | 0.2 | 0.5 | 0.5 | 0.15 | 1.1 | rest | 10 | 0.0 | 0.4 | rest |
| 4 | 0.2 | 2.5 | 0.5 | 0.15 | 1.1 | rest | 10 | 0.0 | 0.4 | rest |
| 5 | 0.2 | 0.0 | 0.5 | 0.15 | 1.1 | rest | 10 | 0.5 | 0.4 | rest |
| 6 | 0.2 | 0.0 | 0.5 | 0.15 | 1.1 | rest | 10 | 1.0 | 0.4 | rest |
| 7 | 0.2 | 0.0 | 0.5 | 0.15 | 1.1 | rest | 10 | 2.0 | 0.4 | rest |
| 8 | 0.2 | 0.0 | 0.5 | 0.15 | 1.1 | rest | 10 | 3.0 | 0.4 | rest |
| 9 | 0.2 | 0.2 | 0.5 | 0.15 | 1.1 | rest | 10 | 1.4 | 0.4 | rest |
| 10 | 0.2 | 0.5 | 0.5 | 0.15 | 1.1 | rest | 10 | 0.2 | 0.4 | rest |
| 11 | 0.2 | 1.2 | 0.5 | 0.15 | 1.1 | rest | 10 | 0.1 | 0.4 | rest |

(Clearance Filling Test)

Figure 2:
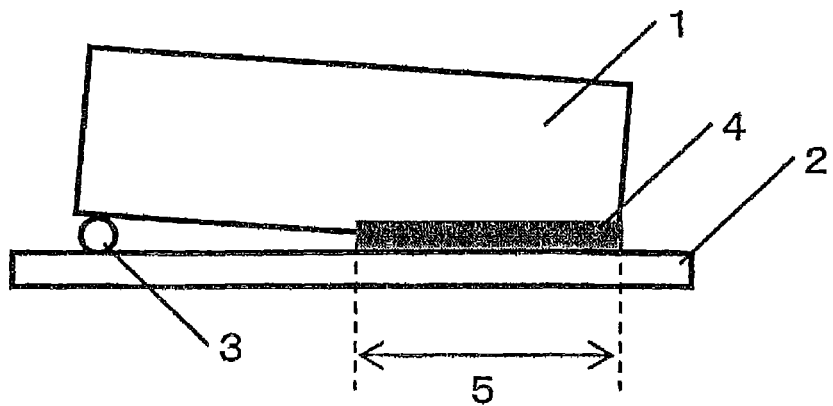
FIG. 2 is an explanatory view to explain a clearance filling test.

The brazeability was evaluated by a clearance filling test, with the test method being shown in FIG. 2. Each brazing sheet fabricated as described above was cut into a size of 70×20 mm, and a horizontal plate (2) was disposed such that its surface including the filler alloy was directed upwards. A vertical plate (1) disposed on the horizontal plate (2) to vertically extend was prepared by cutting a bare sheet specified in JIS A3003 having a thickness of 1.0 mm into a size of 60×20 mm. A stainless wire of φ1.0 mm was used as a spacer (3) for forming a clearance between the horizontal plate (2) and the vertical plate (1), and was disposed at a position 50 mm away from a contact point between the horizontal plate (2) and the vertical plate (1).

In Examples 1 to 3, brazing was carried out in a furnace under an argon gas atmosphere without using flux by employing samples that were fabricated for the clearance filling test as described above. In each of those Examples, three types of brazing process were carried out by employing the brazing sheets Nos. 3, 6 and 10 as the horizontal plates. More specifically, an upper surface of the horizontal plate (2) and an opposing lower surface of the vertical plate (1) were brazed to each other. The oxygen concentration in the furnace was set to be 10, 25, and 50 ppm. The heating for the brazing was carried out while the temperature of the sample for the clearance filling test was measured. First, the sample was heated under such a temperature raising condition that a time required for the temperature of the sample to reach 600° C. was about 10 minutes. Thereafter, the sample was held at 600° C. for 3 minutes, and then taken out from the furnace after cooling it. In Comparative Example 1, the brazing was carried out using the nitrogen gas instead of the argon gas used in Examples 1-3. Table 2 lists the atmosphere gases and the oxygen concentrations in the furnace.

TABLE 2

|  | Atmosphere Gas in Furnace | Oxygen Concentration in Furnace (ppm) | Clearance Filling Length (mm) | | |
| --- | --- | --- | --- | --- | --- |
|  |  |  | Brazing Sheet No. 3 | Brazing Sheet No. 6 | Brazing Sheet No. 10 |
| Example 1 | argon | 10 | 44 | 42 | 45 |
| Example 2 | argon | 25 | 38 | 35 | 39 |
| Example 3 | argon | 50 | 28 | 21 | 26 |
| Comparative Example 1 | nitrogen | 10 | 12 | 10 | 10 |

In the sample after the brazing, a fillet was formed in a state extending toward the spacer (3) from the contact point between the horizontal plate (2) and the vertical plate (1). The length of the fillet (4) from the contact point was measured as a clearance filling length (5). Table 2 lists the clearance filling length (5) for each brazing sheet.

As seen from Table 2, in each of Examples 1 to 3 in which the heating for the brazing was carried out in the argon gas, the clearance filling length was longer than 20 mm and the satisfactory brazeability could be obtained. On the other hand, in Comparative Example 1 in which the heating for the brazing was carried out in the nitrogen gas, the clearance filling length was 12 mm or shorter and the brazeability were inferior.

For the filler alloy subjected to the brazing, respective luminous intensities of a nitrogen atom and an oxygen atom were measured by a glow discharge optical emission spectrometer (with a high-frequency power of 30 W), and the relationship between the sputtering time and the luminous intensity ratio (N/O)nor was examined based on the measurement results. The result obtained with the brazing in the nitrogen gas, shown in FIG. 1, corresponds to Comparative Example 1, and the result obtained with the brazing in the argon gas corresponds to Example 1.

As discussed above, it was found that, in the filler alloy subjected to the brazing in the nitrogen gas, a presence ratio of the nitrogen atom to the oxygen atom near the surface of the filler alloy was larger than that at the interior thereof where the luminous intensity ratio (N/O) was constant. It was hence confirmatively estimated that the film-like reaction product of the metal aluminum and the nitrogen gas, which deteriorates the brazeability, was produced near the surface of the filler alloy. In contrast, it was found that, in the filler alloy subjected to the brazing in the argon gas, a presence ratio of the nitrogen atom to the oxygen atom near the surface of the filler alloy was generally smaller than that at the interior thereof where the luminous intensity ratio (N/O) was constant. It was hence confirmatively estimated that the film-like reaction product of the metal aluminum and the nitrogen gas, which deteriorates the brazeability, was not produced near the surface of the filler alloy.

In Examples 4 to 11, the brazing was carried out in the furnace under an argon gas atmosphere and under a mixed gas atmosphere of argon and nitrogen (volume ratio of argon: nitrogen=1:1) without using flux. The oxygen concentration in the furnace was 10 ppm in each case. The brazing sheets No. 1, 2, 4, 5, 7 to 9, and 11 were used in Examples 4 to 11, respectively. A method of fabricating each brazing sheet, a thickness and a clad ratio of the filler alloy, a method of preparing a sample for the clearance filling test, a testing method, and a manner of measuring the fillet length were the same as those in Example 1. Table 3 lists the clearance filling length in each Example under the argon gas atmosphere and the mixed gas atmosphere.

TABLE 3

|  |  | Clearance Filling Length (mm) | |
| --- | --- | --- | --- |
|  |  | Argon Gas Atmosphere (oxygen concentration in furnace: 10 ppm) | Mixed Gas Atmosphere of Argon and Nitrogen = 1:1 (oxygen concentration in furnace: 10 ppm) |
| Example 4 | Brazing Sheet No. 1 | 26 | 22 |
| Example 5 | Brazing Sheet No. 2 | 40 | 37 |
| Example 6 | Brazing Sheet No. 4 | 37 | 33 |
| Example 7 | Brazing Sheet No. 5 | 40 | 36 |
| Example 8 | Brazing Sheet No. 7 | 38 | 34 |
| Example 9 | Brazing Sheet No. 8 | 28 | 23 |
| Example 10 | Brazing Sheet No. 9 | 40 | 37 |
| Example 11 | Brazing Sheet No. 11 | 43 | 39 |

As seen from Table 3, in every case of Examples 4 to 11, the clearance filling length was longer than 20 mm and the satisfactory brazeability was obtained with the heating for the brazing in both of the argon gas atmosphere and the mixed gas atmosphere.

INDUSTRIAL APPLICABILITY

Good brazeability can be achieved, based on the action of Mg breaking the oxide film, by employing the brazing method of the present invention and by heating the filler alloy in argon gas without using flux. Furthermore, a stable brazeability can be obtained with high reliability and superior industrial applicability.

LIST OF REFERENCE SYMBOLS

1 . . . vertical plate
2 . . . horizontal plate
3 . . . spacer
4 . . . fillet
5 . . . clearance filling length

The invention claimed is:

1. A method for brazing an aluminum member, the method comprising the steps of:
placing a fluxless aluminum member into a furnace, said aluminum member comprising a brazing sheet having a two-layer structure that includes a core made of aluminum or an aluminum alloy, and a filler material made of an aluminum alloy and clad on one outer surface of said core, or having a three-layer structure that includes said filler material clad on two outer surfaces of said core, at least one of said core and said filler material containing Mg, wherein said filler material has an outer surface opposite to an inner surface thereof which is closely contacted with said core, said outer surface of said filler material being exposed to an atmosphere in said furnace and configured to melt at a lower temperature than a melting temperature of said core;
heating said aluminum member in said furnace at a temperature lower than the melting temperature of said core for enabling the brazing of said aluminum member without using flux in an argon gas-containing atmosphere in a state that said outer surface of the filler material is exposed to the argon gas-containing atmosphere; and
controlling the amount of argon gas introduced into the furnace such that, given that a ratio of luminous intensity of a nitrogen atom to luminous intensity of an oxygen atom, measured by glow discharge optical emission spectrometry, is defined as a luminous intensity ratio (N/O) and that the luminous intensity ratio (N/O) indicating a constant value at the interior of said filler material after having been subjected to the brazing is 1.0, the luminous intensity ratio (N/O) near the surface of said filler material up to the depth where said constant value is indicated, is 1.2 or less;
wherein the argon gas-containing atmosphere in said furnace is an argon gas atmosphere or a mixed gas atmosphere of argon gas and nitrogen gas in which a volume of nitrogen gas is less than or equal to a volume of argon gas, and wherein an oxygen concentration in said furnace is 25 ppm or lower.

2. A brazing apparatus used for carrying out the brazing method according to claim 1.

3. A method for brazing an aluminum member according to claim 1, wherein the ratio in the volume of argon gas to that of the nitrogen gas is 1:1 in the mixed gas atmosphere.

4. The method according to claim 1, wherein internal components of the furnace which are contacted by argon gas comprise carbon.

5. The method of claim 1, further comprising steps of evacuating the furnace after introducing the object to be brazed into the furnace, and then introducing the argon gas-containing atmosphere into the furnace prior to the heating step.

6. A method for brazing an aluminum member, the method comprising the steps of:
a) introducing first and second aluminum members arranged in contact with one another into a furnace, said first aluminum member comprising a brazing sheet having a two-layer structure that includes a core made of aluminum or an aluminum alloy, and a meltable outer cladding made of an aluminum alloy and clad on one outer surface of said core, or having a three-layer structure that includes said meltable outer cladding clad on two outer surfaces of said core, at least one of said core and said outer cladding containing Mg, wherein said outer cladding is configured to melt at a lower temperature than a melting temperature of said core;
b) evacuating the furnace by removing ambient air therefrom;
c) introducing an argon gas-containing atmosphere into said furnace, the argon gas-containing atmosphere being either an argon gas atmosphere or a mixed gas atmosphere comprising argon gas and nitrogen gas in which a volume of nitrogen gas is less than or equal to a volume of argon gas, and wherein an oxygen concentration 25 ppm or lower, whereby an outer surface of said outer cladding opposite to an inner surface thereof which is closely contacted with said core is exposed to said argon gas-containing atmosphere in said furnace; and
d) heating said first and second aluminum members in said furnace to a brazing temperature lower than the melting temperature of said core, at which brazing temperature melting of the outer cladding occurs, whereby said aluminum members are joined by brazing.

7. The method according to claim 6, wherein internal components of the furnace which are contacted by argon gas comprise carbon.

8. The method according to claim 1, wherein the filler material comprises Mg.

9. The method according to claim 6, wherein the outer cladding comprises Mg.

* * * * *